(12) United States Patent
Lawyer et al.

(10) Patent No.: US 8,071,285 B1
(45) Date of Patent: Dec. 6, 2011

(54) ZINC FINGER PROTEIN DERIVATIVES AND METHODS OF USING SAME

(76) Inventors: Carl Henry Lawyer, Springfield, IL (US); Matthew Carl Lawyer, Springfield, IL (US); Edward Zadok Lawyer, Tucson, AZ (US)

( * ) Notice: Subject to any disclaimer, the term of this patent is extended or adjusted under 35 U.S.C. 154(b) by 288 days.

(21) Appl. No.: 10/843,200

(22) Filed: May 11, 2004

Related U.S. Application Data

(60) Provisional application No. 60/470,275, filed on May 14, 2003.

(51) Int. Cl.
*A61K 33/22* (2006.01)
*A61K 38/03* (2006.01)

(52) U.S. Cl. ............ 435/6; 424/614; 514/15; 514/12; 514/2

(58) Field of Classification Search .............. None
See application file for complete search history.

(56) References Cited

U.S. PATENT DOCUMENTS

| | | | |
|---|---|---|---|
| 6,140,081 A | 10/2000 | Barbas | 435/69.1 |
| 6,140,466 A | 10/2000 | Barbas, III et al. | 530/350 |
| 6,242,568 B1 | 6/2001 | Barbas, III et al. | 530/350 |
| 6,534,261 B1 * | 3/2003 | Cox et al. | 435/6 |
| 2002/0076393 A1 | 6/2002 | Fehlbaum et al. | 424/85.1 |
| 2003/0037355 A1 * | 2/2003 | Barbas et al. | 800/278 |

OTHER PUBLICATIONS

Laity et al. Current Opinion in Structural Biology. 2001;11:39-46.*
Berkhout et al. AIDS Research and Human Retroviruses. Volume 18, No. 2, 2002, pp. 133-141.*
Fröhlich et al. (Biology of Reproduction. 2001; 64: 1072-1079).*
Choo et al. (Current Opinion in Structural Biology. 2000; 10: 411-416).*
Martin et al. (Tetrahedron. 2000; 56: 9451-9460).*
Russo et al (Molecular and Cellular Biology. Nov. 1993; 13(11): 6858-6865).*
Beerli, et al., "Engineering polydactyl zinc-finger transcription factors", Nature Biotechnology, Feb. 2002, vol. 20, No. 2, pp. 135-141.
Choo, et al., "Toward a code for the interactions of zinc fingers with DNA: Selection of randomized fingers displayed on phage", Proc. Natl. Acad. Sci. USA, Nov. 8, 1994, vol. 91, No. 23, pp. 11163-11167.
Choo, et al. "In vivo repression by a site-specific DNA-binding protein designed against an oncogenic sequence", Nature, Dec. 15, 1994, vol. 372, pp. 642-645.
Desjarlais, et al., "Length-encoded multiplex binding site determination: Application to zinc finger proteins", Proc. Natl. Acad. Sci. USA, Nov. 1994, vol. 91, pp. 11099-11103.
Greisman, et al., "A General Strategy for Selecting High-Affinity Zinc Finger Proteins for Diverse DNA Target Sites", Science, Jan. 31, 1997, vol. 275, pp. 657-661.
Jamieson, et al., "In Vitro Selection of Zinc Fingers with Altered DNA-Binding Specificity", Biochemistry, 1994, vol. 33, pp. 5689-5695.
Kang, et al., "Zinc Finger Proteins as Designer Transcription Factors", The Journal of Biological Chemistry, Mar. 24, 2000, vol. 275, No. 12, pp. 8742-8748.
Rebar, et al., "Zinc Finger Phage: Affinity Selection of Fingers with New DNA-Binding Specificities", Feb. 4, 1994, vol. 263, No. 5147, pp. 671-673.
Wu, et al., "Building zinc fingers by selection: Toward a therapeutic application", Proc. Natl. Acad. Sci. USA, Jan. 1995, vol. 92, pp. 344-348.

\* cited by examiner

*Primary Examiner* — Scott Long
(74) *Attorney, Agent, or Firm* — McDonnell Boehnen Hulbert & Berghoff LLP

(57) ABSTRACT

The present invention provides zinc finger nucleotide binding polypeptide variants that have at least three zinc finger modules that bind to a target cellular nucleotide sequence and modulate the transcriptional function of the cellular nucleotide sequence.

2 Claims, No Drawings

ZINC FINGER PROTEIN DERIVATIVES AND METHODS OF USING SAME

CROSS REFERENCE TO RELATED APPLICATION

This application claims priority from U.S. Provisional Application Ser. No. 60/470,275, filed May 14, 2003.

BACKGROUND OF THE INVENTION

1. Field of the Invention

This invention relates generally to the field of gene therapy and more particularly to the production and use of defensin polypeptide zinc finger-nucleotide binding and linker motifs.

2. Description of Related Art

Defensins are cationic, cysteine-rich peptides that display broad spectrum antimicrobial activity. Their structure is characterized by a conserved cysteine motif that forms three disulfide linkages, imposing a characteristic β-sheet structure (Hill et al., 1991; White et al., 1995). Associated with this structure is an amphiphilic charge distribution that enables the defensins to interact with and disrupt target cell membranes (Lehrer et al., 1989). This disruption is thought to be accomplished by the formation of channels in the target membrane, leading to cell lysis (Kagan et al., 1990). Defensins have been shown to inhibit proliferation of both gram-positive and gram-negative bacteria, yeast and numerous viruses. In particular, defensins inhibit the proliferation of the yeast strain *Candida albicans* and the gram-negative bacteria *Escherichia coli* (Porter et al., 1997; Harder et al., 1997; Schonwetter et al., 1995; Daher et al., 1986).

Defensins have recently been identified as an integral component of the antimicrobial barrier of mucosal surfaces. In both the human and murine small intestine, defensin RNA has been localized to the Paneth cell, a specialized epithelial cell located at the crypt base (Ouellette et al., 1989; Jones et al., 1992). The associated peptide has been localized within secretory granules of the Paneth cell and in the lumen of the small intestine, suggesting a role for defensins in host defense in the gut (Selsted et al., 1992). Defensins have also been found in bovine and human respiratory epithelium. Tracheal antimicrobial peptide, a β-defensin isolated from bovine tracheal mucosa, was localized to the ciliated columnar epithelial cells of the trachea and bronchi (Diamond et al., 1991; Diamond et al., 1993). Lingual antimicrobial peptide, another β-defensin, was found in bovine lingual mucosa and stratified squamous epithelium of the tongue (Schonwetter et al., 1995). Most recently, human β-defensin-1 was demonstrated to be present in the epithelium of the trachea and bronchi, as well as the submucosal gland and alveolar epithelium (Goldman et al., 1997; Zhao et al., 1996).

Considerable data exists indicating that epithelial defensins are up-regulated in response to infection. In cultured tracheal epithelial cells, tracheal antimicrobial peptide message is induced following exposure to bacterial lipopolysaccharide (Diamond et al., 1996). This induction was blocked by antibody to CD14, suggesting that epithelial cells provide an active, inducible antimicrobial defense. Following injury to bovine tongue, lingual antimicrobial peptide RNA message increased at the site of injury (Schonwetter et al., 1995). Induction of lingual antimicrobial peptide was also observed following acute infection in bronchial epithelium and chronic infection in ileal mucosa (Stolzenberg et al., 1997). Together these data support a role for β-defensins as important host defense effector molecules that are rapidly mobilized by epithelium upon injury or infection.

Due to the significant host defense properties of defensins, any means which stimulates or induces the production of these peptides is desired.

The foregoing discussion of the prior art is taken largely from published U.S. Patent Application No. 2002/0076393 to Fehlbaum et al., who propose a method of increasing the production of defensins in eukaryotic cells by exposing the eukaryotic cells to a composition comprising isoleucine or active isomers or analogs thereof in an amount sufficient to effect the desired increase.

SUMMARY OF THE INVENTION

The present invention provides for the production of zinc fingers defensin protein sequences to increase or decrease expression of host and/or pathogen gene sequences for treating numerous diseases.

The present invention is based in part on our discovery of and design of defensin polypeptide sequences which encode zinc finger binding motifs for use in controlling gene transcription and translation, together with methods of designing zinc finger defensin polypeptides for binding to a particular target DNA or RNA sequence and, inter alia, use of designed zinc finger defensin polypeptides for various in vitro or in vivo applications. More particularly, our invention is based on the premises that:

1) defensins are in reality zinc finger peptides; and
2) defensins act directly as zinc finger peptides on DNA and RNA and other zinc finger peptides, to control gene expression. While not wishing to be bound by theory, it is believed that zinc finger defensin protein sequences represent ideal zinc finger defensin protein sequences to increase or decrease expression of host and/or pathogen gene sequences in the most ideal way for survival of the host. The defensin zinc finger represents as few as one single zinc finger or even a "half-finger" able to increase or decrease expression of host and/or pathogen gene sequences in the most ideal way for survival of the host.

The invention also provides a pharmaceutical composition comprising a therapeutically effective amount of a zinc finger defensin polypeptide with a zinc finger linker, in combination with a pharmaceutically acceptable carrier. Pharmaceutical compositions containing one or more of the zinc finger-nucleotide binding polypeptide variants described herein are useful in the therapeutic methods of the invention.

DETAILED DESCRIPTION OF THE INVENTION

Genetic engineering can produce organisms with improved innate immunity to pathogens by inserting defensin genes with zinc finger defensin protein sequences specifically designed to target important pathogens. The signal peptide sequence of the defensin is believed to be the ideal signal peptide sequence for delivery of the defensin to increase or decrease expression of host and/or pathogen gene sequences in the most ideal way for survival of the host.

Transcriptional regulation is primarily achieved by the sequence-specific binding of proteins to DNA and RNA. Of the known protein motifs involved in the sequence specific recognition of DNA, the zinc finger protein is unique in its modular nature. To date, zinc finger proteins have been identified which contain between 2 and 37 modules. More than two hundred proteins, many of them transcription factors, have been shown to possess zinc fingers domains. Zinc fingers connect transcription factors to their target genes mainly by binding to specific sequences of DNA base pairs—the "rungs" in the DNA "ladder".

Zinc finger modules are approximately 30 amino acid-long motifs found in a wide variety of transcription regulatory proteins in eukaryotic organisms. As the name implies, this nucleic acid binding protein domain is folded around a zinc ion. The zinc finger domain was first recognized in the transcription factor TFIIIA from *Xenopus* oocytes (Miller et al., EMBO, 4: 1609-14, 1985; Brown et al., FEBS Lett., 186: 271-74, 1985). This protein consists of nine imperfect repeats of a consensus sequence: (Tyr, Phe)-Xaa-Cys-Xaa$_{2-4}$-Cys-Xaa$_3$-Phe-Xaa$_6$-Leu-Xaa$_2$-His-Xaa$_{3-4}$-His-Xaa$_{2-6}$ (SEQ ID NO: 1) where Xaa is an amino acid.

Like TFIIIA, most zinc finger proteins have conserved cysteine and histidine residues that tetrahedrally-coordinate the single zinc atom in each finger domain. The structure of individual zinc finger peptides of this type (containing two cysteines and two histidines) such as those found in the yeast protein ADR1, the human male associated protein ZFY, the HIV enhancer protein and the *Xenopus* protein Xfin have been solved by high resolution NMR methods (Kochoyan et al., Biochemistry, 30: 3371-86, 1991; Omichinski et al., Biochemistry, 29: 9324-34, 1990; Lee et al., Science, 245: 635-37, 1989) and detailed models for the interaction of zinc fingers and DNA have been proposed (Berg, 1988; Berg, 1990; Churchill et al., 1990). Moreover, the structure of a three finger polypeptide-DNA complex derived from the mouse immediate early protein zif268 (also known as Krox-24) has been solved by x-ray crystallography (Pavletich and Pabo, Science, 252: 809-17, 1991). Each finger contains an antiparallel β-turn, a finger tip region and a short amphipathic α-helix which, in the case of zif268 zinc fingers, binds in the major groove of DNA. In addition, the conserved hydrophobic amino acids and zinc coordination by the cysteine and histidine residues stabilize the structure of the individual finger domain.

While the prototype zinc finger protein TFIIIA contains an array of nine zinc fingers which binds a 43 bp sequence within the 5S RNA genes, regulatory proteins of the zif268 class (Krox-20, Sp1, for example) contain only three zinc fingers within a much larger polypeptide. The three zinc fingers of zif268 each recognize a 3 bp subsite within a 9 bp recognition sequence. Most of the DNA contacts made by zif268 are with phosphates and with guanine residues on one DNA strand in the major groove of the DNA helix. In contrast, the mechanism of TFIIIA binding to DNA is more complex. The amino-terminal 3 zinc fingers recognize a 13 bp sequence and bind in the major groove. Similar to zif268, these fingers also make guanine contacts primarily on one strand of the DNA. Unlike the zif268 class of proteins, zinc fingers 4 and 6 of TFIIIA each bind either in or across the minor groove, bringing fingers 5 and 7 through 9 back into contact with the major groove (Clemens et al., Proc. Natl. Acad. Sci. USA, 89: 10822-826, 1992).

The crystal structure of zif268, indicates that specific histidine (non-zinc coordinating his residues) and arginine residues on the surface of the α-helix participate in DNA recognition. Specifically, the charged amino acids immediately preceding the α-helix and at helix positions 2, 3, and 6 (immediately preceding the conserved histidine) participate in hydrogen bonding to DNA guanines Similar to finger 2 of the regulatory protein Krox-20 and fingers 1 and 3 of Sp1, finger 2 of TFIIIA contains histidine and arginine residues at these DNA contact positions; further, each of these zinc fingers minimally recognizes the sequence GGG. Finger swap experiments between transcription factor Sp1 and Krox-20 have confirmed the 3-bp zinc finger recognition code for this class of finger proteins (Nardelli et al., Nature, 349: 175-78, 1989). Mutagenesis experiments have also shown the importance of these amino acids in specifying DNA recognition.

Zinc finger proteins have also been reported which bind to RNA. Clemens et al., (Science, 260: 530, 1993) found that fingers 4 to 7 of TFIIIA contribute 95% of the free energy of TFIIIA binding to 5S rRNA, whereas fingers 1 to 3 make a similar contribution in binding the promoter of the 5S gene. Comparison of the two known 5S RNA binding proteins, TFIIIA and p43, reveals few homologies other than the consensus zinc ligands (C and H), hydrophobic amino acids and a threonine-tryptophan-threonine triplet motif in finger 6.

Naturally occurring zinc finger defensin protein sequences and subsequences and motifs provide a method of design to produce zinc finger defensins to upregulate or downregulate expression of any desired gene. By way of example, defensin polypeptides such as Epididymal Protein 2 contain a linker region of 5 amino acids HTGEK (SEQ ID NO: 2) identical to the pentapeptide sequence, HTGEK (SEQ ID NO: 2) linker sequence found between zinc fingers 1-2 and 2-3 of transcription Factor IIIB, and also found in Kruppel, Zif268, and many other zinc finger proteins. The conserved HTGEK (SEQ ID NO: 2) linker functions to correctly position two adjacent zinc fingers deep into the major groove of the DNA or RNA helix so their basic amino acid side chains can through the major groove recognize and bind to the DNA or RNA sequence being recognized.

Previously, zinc finger delivery to site of action as an antimicrobial or even an anti-cancer agent have had serious defects:

- The zinc fingers break down very quickly with exposure to air (oxidizing atmosphere), this possibly being why no prokaryotes use zinc fingers, and why retroviruses do not have respiratory spread.
- Relatively minor changes in pH may break down the zinc fingers through unbinding and loss of zinc very quickly (the side chain pK of both histidine and cysteine are the closest to physiological pH range ~7.40+/−0.02 of any of the amino acids).
- Zinc fingers (other than the defensin zinc fingers), in the genome in transcription factor genes are difficult/impossible to utilize therapeutically as there is no method for appropriate regulation of expression and delivery to active site for therapy.

The defensin system essentially is 'built by nature' to deliver active defensin zinc fingers directly to sites of infection in an effective manner. The defensins are known to be routed through the cell by their signal peptide and then cleaved by the protease (usually in beta-defensins at the VR concensus protease cleavage site) as they are activated and secreted and arrive at the battle scene with the invading microbe/mycoplasm/chlamydia/virus/parasite/cancer cell.

The protease that produces proteolytic activation of defensins is called matrix metalloproteinase-7 (MMP-7; matrilysin). Ghosh et al., "Paneth cell trypsin is the processing enzyme for human defensin-5," Nat. Immunol. 3(6): 583-90, 2002. By acting as a prodefensin convertase in human Paneth cells, trypsin is involved in the regulation of innate immunity in the small intestine. Ayabe et al., "Activation of Paneth cell alpha-defensins in mouse small intestine," J. Biol. Chem. 277(7): 5219-28, 2002. MMP-7-dependent procryptdin activation in vivo provides mouse Paneth cells with functional peptides for apical secretion into the small intestine lumen.

Thus, one aspect of our invention is based on our discovery that single defensin molecules are each two zinc fingers linked by a linker sequence, which permits us to modulate the binding and function of other zinc finger proteins as well as to directly bind to DNA and RNA, all resulting in specific control of gene transcription. Accordingly, defensin polypeptide sequences (including both the ~800 known published distinct defensin sequences as well as newly designed defensin polypeptide sequences) encode zinc finger linker and binding motifs for use in sequence specific binding to DNA and RNA and to other proteins and in transcriptional repression and in suppression of neoplastic cell growth and in suppression of pathogen growth.

The present invention allows use of the known ~800 different defensin sequences and >5250 different zinc finger sequences to design zinc finger peptides. More particularly, the invention provides criteria and methods for making new and unique zinc finger defensin proteins specifically designed to target important genes by substituting the DNA Recognition domains of the zinc finger (for example from the 5250 different zinc finger protein sequences) into the 800 different defensin protein sequences), which method specifies (5250×800)=>4,224,000 new unique zinc finger defensin proteins. The invention thus provides criteria and methods for selecting optimum zinc finger defensin protein sequence and DNA or RNA subsequence(s) from a target gene for targeting by zinc finger defensin protein sequence.

We also have discovered the presence of two defensin sequences flanking the Nascent polypeptide-Associated Complex (NAC) domain region of basic transcription Factor III, to modulate gene expression on a sequence-specific basis. A ten amino acid region important in sequence specific DNA and RNA binding in the defensin HBD1 sequence TCYRGKAKCC (SEQ ID NO: 3) is identical to the gyrase-flanking sequence. NAC is a multifunctional eukaryotic protein that is involved in translation and subcellular targeting of nascent polypeptides (Wang et al., 1995; Wickner, 1995; Powers and Walter, 1996) but it has been shown to function also as a transcription coactivator (Yotov et al., 1998). The gyrase region is the "NAC domain" [pfam01849], a domain found in the archaeal and eukaryotic Basic Transcription Factor proteins involved in translation and transcription.

Our discovery solves the problem of zinc finger delivery to site of action. With our discovery, simply using standard gene therapy techniques to insert an additional defensin gene (with the DNA or RNA helix recognition sites in the defensin designed to attack any desired pathogen, for example the SARS coronavirus) in the genome adjacent to, for example, the tracheal antimicrobial peptide gene, and including the upstream and downstream regulatory DNA sequences, should result in appropriate expression/delivery/activation of the new defensin to eradicate the pathogen in the tracheal and bronchi, for example, SARS coronavirus. There are a variety of well-characterized beta defensins secreted in and onto all body surfaces to use in a similar technique to resist any pathogen at any site.

This technique can be used to generate transgenic livestock resistant to any specified livestock disease with elimination of need for vaccination including in all subsequent generations of the livestock or humans.

While not wishing to be bound by theory, it is postulated that the defensin zinc finger polypeptides control transcription through acting as heterodimers to modulate the previously described heterodimerization interaction of NAC with the transcription factor BTF3b (Wiedmann et al., Nature 370: 434-40, 1994).

As used herein, a zinc finger-nucleotide binding polypeptide "variant" refers to a polypeptide which is a mutagenized form of a zinc finger protein or one produced through recombination. A variant may be a hybrid which contains zinc finger domain(s) from one protein linked to zinc finger domain(s) of a second protein, for example. The domains may be wild type or mutagenized. A "derivative" includes a truncated form of a wild type zinc finger protein, which contains less than the original number of fingers in the wild type protein. A derivative also includes variant zinc finger polypeptides. Examples of zinc finger-nucleotide binding polypeptides from which a derivative or variant may be produced include TFIIIA and zif268.

A "zinc finger-nucleotide binding motif" refers to any two or three-dimensional feature of a nucleotide segment to which a zinc finger-nucleotide binding derivative polypeptide binds with specificity. Included within this definition are nucleotide sequences, generally of five nucleotides or less, as well as the three dimensional aspects of the DNA double helix, such as the major and minor grooves, the face of the helix, and the like. The motif is typically any sequence of suitable length to which the zinc finger polypeptide can bind. For example, a three finger polypeptide binds to a motif typically having about 9 to about 14 base pairs. Therefore, the invention provides zinc finger-nucleotide binding polypeptides of any specificity, and the zinc finger binding motif can be any sequence designed by the experiment or to which the zinc finger protein binds. The motif may be found in any DNA or RNA sequence, including regulatory sequences, exons, introns, or any non-coding sequence.

The zinc finger-nucleotide binding polypeptide variant of the invention comprises at least two zinc finger modules that bind to a cellular nucleotide sequence and modulate the function of the cellular nucleotide sequence. The term "cellular nucleotide sequence" refers to a nucleotide sequence which is present within the cell. It is not necessary that the sequence be a naturally occurring sequence of the cell. For example, a retroviral genome which is integrated within a host's cellular DNA, would be considered a "cellular nucleotide sequence". The cellular nucleotide sequence can be DNA or RNA and includes both introns and exons. The cell and/or cellular nucleotide sequence can be prokaryotic or eukaryotic, including a yeast, virus, or plant nucleotide sequence.

In the practice of this invention it is not necessary that the zinc finger-nucleotide binding motif be known in order to obtain a zinc-finger nucleotide binding variant polypeptide. While the present invention describes zinc finger proteins identified only in eukaryotes, it also is contemplated that zinc finger-nucleotide binding motifs can be identified in non-eukaryotic DNA or RNA, especially in the native promoters of bacteria and viruses by the binding thereto of the genetically modified isolated constructs of this invention that preserve the well known structural characteristics of the zinc finger, but differ from zinc finger proteins found in nature by their method of production, as well as their amino acid sequences and three-dimensional structures.

The characteristic structure of the known wild type zinc finger proteins are made up of from two to as many as 37 modular tandem repeats, with each repeat forming a "finger" holding a zinc atom in tetrahedral coordination by means of a pair of conserved cysteines and a pair of conserved histidines. Generally each finger also contains conserved hydrophobic amino acids that interact to form a hydrophobic core that helps the module maintain its shape.

The term "modulate" refers to the suppression, enhancement or induction of a function. For example, the zinc finger-nucleotide binding polypeptide variant of the invention may modulate a promoter sequence by binding to a motif within the promoter, thereby enhancing or suppressing transcription of a gene operatively linked to the promoter cellular nucleotide sequence. Alternatively, modulation may include inhibition of transcription of a gene where the zinc finger-nucleotide binding polypeptide variant binds to the structural gene and blocks DNA dependent RNA polymerase from reading through the gene, thus inhibiting transcription of the gene. The structural gene may be a normal cellular gene or an oncogene, for example.

The promoter region of a gene includes the regulatory elements that typically lie 5' to a structural gene. If a gene is to be activated, proteins known as transcription factors attach to the promoter region of the gene. This assembly resembles an "on switch" by enabling an enzyme to transcribe a second genetic segment from DNA into RNA. In most cases the resulting RNA molecule serves as a template for synthesis of a specific protein; sometimes RNA itself is the final product.

The promoter region may be a normal cellular promoter or, for example, an onco-promoter. An onco-promoter is generally a virus-derived promoter. For example, the long terminal repeat (LTR) of retroviruses is a promoter region which may be a target for a zinc finger binding polypeptide variant of the invention. Promoters from members of the Lentivirus group, which include such pathogens as human T-cell lymphotrophic virus (HTLV) 1 and 2, or human immunodeficiency virus (HIV) 1 or 2, are examples of viral promoter regions which may be targeted for transcriptional modulation by a zinc finger binding polypeptide of the invention.

The zinc finger-nucleotide binding polypeptide derivatives or variants of the invention include polypeptides that bind to a cellular nucleotide sequence such as DNA, RNA or both. A zinc finger-nucleotide binding polypeptide which binds to DNA, and specifically, the zinc finger domains which bind to DNA, can be readily identified by examination of the "linker" region between two zinc finger domains. The linker amino acid sequence TGEK(P) (SEQ ID NO: 4) is typically indicative of zinc finger domains which bind to a DNA sequence. Therefore, one can determine whether a particular zinc finger-nucleotide binding polypeptide preferably binds to DNA or RNA by examination of the linker amino acids.

Additionally, the signal peptide sequence can include a mitochondrial or perioxisome targeting signal in the defensin to target or deliver the zinc finger defensin protein sequence into the mitochondria or perioxisome where the defensin zinc fingers can interact with and bind to the DNA or RNA in the mitochondria or perioxisome to produce the desired effect, such as apoptosis.

The defensin zinc finger-containing compositions of the present invention can usefully be administered to mammals in novel topical and intravenous and intramuscular and subcutaneous and oral compositions at dosage levels to elicit a systemic therapeutic response and provide enhanced bioavailability, minimize variations in blood levels, and achieve more rapid onset of activity, persistence of activity, ease of administration, and reduced side effects as compared to conventional gene therapy methods of administration of zinc finger proteins.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like which would be to a degree that would prohibit administration of the composition.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use also can be prepared. The preparation also can be emulsified.

The active ingredient can be mixed with excipients which are pharmaceutically acceptable and compatible with the active ingredient and in amounts suitable for use in the therapeutic methods described herein. Suitable excipients are, for example, sterile water, saline, dextrose, glycerol, ethanol or the like and combinations thereof. In addition, if desired, the composition can contain minor amounts of auxiliary substances such as wetting or emulsifying agents, as well as pH buffering agents and the like which enhance the effectiveness of the active ingredient.

The therapeutic pharmaceutical composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups also can be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

DETAILED DESCRIPTION OF PREFERRED EMBODIMENTS

The invention in one aspect includes a nucleotide sequence encoding a zinc finger-nucleotide binding polypeptide variant. DNA sequences encoding the zinc finger-nucleotide binding polypeptides of the invention, including native, truncated, and expanded polypeptides, can be obtained by several methods. For example, the DNA can be isolated using hybridization procedures which are well known in the art. These include, but are not limited to: (1) hybridization of probes to genomic or cDNA libraries to detect shared nucleotide sequences; (2) antibody screening of expression libraries to detect shared structural features; and (3) synthesis by the polymerase chain reaction (PCR). RNA sequences can be obtained by methods known in the art (see, for example, Current Protocols in Molecular Biology, Ausubel, et al. eds., 1989).

More particularly, the development of specific DNA sequences encoding zinc finger-nucleotide binding proteins of the invention can be obtained by: (1) isolation of a double-stranded DNA sequence from the genomic DNA; (2) chemical manufacture of a DNA sequence to provide the necessary codons for the polypeptide of interest; and (3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA is the least used. This is especially true when it is desirable to obtain the microbial expression of mammalian polypeptides due to the presence of introns.

For obtaining zinc finger derived-DNA binding polypeptides in accordance with the present invention, the synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the formation of cDNA sequences. Among the standard procedures for isolating cDNA sequences of interest is the formation of plasmid-carrying cDNA libraries which are derived from reverse transcription of mRNA which is abundant in donor cells that have a high level of genetic expression.

A defensin can be designed using the method of the present invention to interact with target DNA for any known site recognized by known zinc finger proteins. It can further be designed to bind and recognize any desired DNA or RNA sequence when the "code" is fully worked out (currently only partially known) for which amino acid sequences and which helical peptide regions recognize and interact with which specific DNA sequences. The preferred method is to change the defensin helical regions recognizing and interacting with specific DNA sequences from those of the defensin to those of the zinc finger recognizing and interacting with specific DNA sequences.

The invention now will be illustrated by the following non-limiting Examples:

Example 1

Antifungal Pyrimidine Pathway Suppressor of Pyrimidine Induction

Pyrimidine Pathway Regulator was chosen for the design of our working model of inhibitor because no known human homolog is known to exist, so toxicity to human cells is unlikely.

The sequence of the known Pyrimidine Pathway Regulator is: MKSRTACKRCRLKKIKCDQEFPSCK-RCAKLEVPCVSLDPATGKDVPRSYVFFLEDRL AVM-MRVLKEYGVDPTKIRGNIPATSDDEPFDLKKYSSVS (SEQ ID NO: 5).

The zinc finger region of the transcription factor known as "Gal4" has known sequence: CDICRLKKLKCSKEKPK-CAKCLKNNWEC (SEQ ID NO: 6), and the helical regions interacting with DNA are known to be DICRLK (SEQ ID NO: 7) and AKCLKN (SEQ ID NO: 8).

The sequence of the epididymal protein 2 [EP2] defensin that we discovered contains the HSGEK (SEQ ID NO: 9) consensus zinc finger linker sequence (AF168617_1 HE2 beta1 [Homo sapiens] gi|10799276|gb|AAG21881.1|sperm associated antigen 11, isoform D precursor) is: CRMQQGI-CRLFFCHSGEKKRDICSDPWNRCC (SEQ ID NO: 10).

Our Antifungal Pyrimidine Pathway Suppressor was designed by swapping the amino acid sequence of the two helical regions DICRLK (SEQ ID NO: 7) and AKCLKN (SEQ ID NO: 8) of the known Pyrimidine Pathway Regulator zinc finger interacting with DNA with the corresponding regions GQCLYS (SEQ ID NO: 11) and GTCYRG (SEQ ID NO: 12) of the defensin HBD1 and with the HSGEK linker region of the defensing CRMQQGICRLFFCHSGEKKRDICSDPWNRCC (SEQ ID NO: 10) resulting in our Antifungal Pyrimidine Pathway Suppressor amino acid sequence: GLGHRSDHYNCVSSGDICRLKACHSGEKIQAKCLKNKAKCCK (SEQ ID NO: 13).

Our Antifungal Pyrimidine Pathway Suppressor was assembled using standard gene assembly techniques to change the defensin [HBD2] helical regions interacting with DNA from those of HBD2 to those of the Pyrimidine Pathway Regulator. Thus a new Antifungal Pyrimidine Pathway Suppressor will recognize and bind to the Pyrimidine Pathway Regulator binding sites and act to stop pyrimidine synthesis and have useful antifungal activity.

Our Antifungal Pyrimidine Pathway Suppressor: GLGHRSDHYNCVSSGDICRLKACHSGEKIQAKCLKNKAKCCK (SEQ ID NO: 13)

Human beta defensin1: MRTSYLLLFTLCLLLSEMASGGNFLTGLGHRSDHYNCVSSGGQCLYSACPIFTKIQGTCYRGKAKCCK (SEQ ID NO: 14)

Human beta defensin2: MRVLYLLFSFLFIFLMPLPGVFGGIGDPVTCLKSGAICHPVFCPRRYKQIGTCGLPGTKCCKKP (SEQ ID NO: 15)

EP2 Sperm Associated Antigen Defensin: CRMQQGICRLFFCHSGEKKRDICSDPWNRCC (SEQ ID No: 10)

Zinc finger of Pyrimidine Pathway Regulator: CKRCRLKKIKCDQEFPSCKRCAKLEVPCV (SEQ ID NO: 16)

Zinc finger of Ga14 transcription factor: CDICRLKKLKCSKEKPKCAKCLKNNWEC (SEQ ID NO: 6)

Example 2

Yeast Induction

Similar domain swaps into defensin zinc finger proteins can be made using other transcriptional control factors to block expression of their target gene: Pyrimidine Pathway Suppressor; Marmorstein et al., "Crystal structure of a PPR1-DNA complex: DNA recognition by proteins containing a Zn2Cys6 binuclear cluster," Genes Dev. 8(20): 2504-12, 1994.

PPR1 is a yeast transcription factor that contains a six-cysteine, two-zinc (Zn) domain, homologous to a similar structure in GAL4. Like GAL4, it binds to DNA sites with conserved CGG triplets symmetrically placed near each end. Whereas the GAL4 site has 11 intervening base pairs, the PPR1 site has 6. The crystal structure of a 95-residue fragment of PPR1 in specific complex with DNA shows that the protein binds to a symmetrical 14-bp recognition site as a nonsymmetrical homodimer. An amino-terminal Zn domain interacts with a conserved CGG triplet near each end of the site through major groove contacts, and the carboxy-terminal residues mediate dimerization through a coiled-coil element and an extended strand. A linker region, connecting the Zn domain and the coiled-coil, folds into a beta-hairpin. This hairpin packs differently on the two subunits and leads to a striking asymmetry, which is largely restricted to the dimerization and linker regions of the protein. Comparison with the GAL4-DNA structure shows that their specificities for sites of different length are determined by the preferred folds of their respective linker segments and by residues at the amino-terminal ends of their coiled-coils. None of these residues contact DNA in PPR1, and they contact only the sugar phosphate backbone in GAL4. This novel mode of DNA site selection is employed by other proteins that contain a Zn2Cys6 binuclear cluster.

Example 3

Evolution of a Fungal Regulatory Gene Family

The Zn(II)2Cys6 Binuclear Cluster DNA Binding Motif

The coevolution of DNA binding proteins and their cognate binding sites reportedly is essential for the maintenance of function (see Todd et al., Fungal Genet. Biol. 21(3): 388-405, 1997). As a result, comparison of DNA binding proteins of unknown function in one species with characterized DNA binding proteins in another can identify potential targets and functions. The Zn(II)2Cys6 (or C6 zinc) binuclear cluster DNA binding domain has thus far been identified exclusively in fungal proteins, generally transcriptional regulators, and there are more than 80 known or predicted proteins which contain this motif, the best characterized of which are GAL4, PPR1, LEU3, HAP1, LAC9, and PUT3. Here we review all known proteins containing the Zn(II)2Cys6 motif, along with their function, DNA binding, dimerization, and zinc(II) coordination properties and DNA binding sites. In addition, we have identified all of the Zn(II)2Cys6 motif-containing proteins in the sequence databases, including a large number with unknown function from the completed *Saccharomyces cerevisiae* and ongoing *Schizosaccharomyces pombe* genome projects, and examined the phylogenetic relationships of all the Zn(II)2Cys6 motifs from these proteins. Based on these relationships, we have assigned potential functions to a number of these unknown proteins.

Example 4

Defensin Polypeptides Capable of Controlling Zinc Finger Proteins' Binding to Diverse DNA Target Sites There is direct interaction of all defensins including defensins containing SGEK (SEQ ID NO: 17) and TGEK (SEQ ID NO: 18) with DNA and RNA, these interactions producing modulation of gene transcription. The conserved TGEK (SEQ ID NO: 18) tetrapeptide in finger II of TFIIIA is required for DNA binding. A Gly-dependent bend structure and a terminal positive charge in this tetrapeptide are important for TFIIIA interaction with DNA. The TGEK (SEQ ID NO: 18) or SGEK (SEQ ID NO: 17) sequence is associated with major DNA helix groove binding fingers. We have discovered that the defensins are able on a DNA/RNA sequence specific basis to interfere with the discontinuous winding in the major groove (of DNA or RNA) that transcription factors and other zinc-finger proteins engage in to modulate gene transcription based on recognition of separated DNA or RNA sequences. Thus we have discovered sequence-specific control of gene transcription by defensin proteins. This allows explicit and convenient control of the expression of any and all genes, a powerful tool for all branches of science.

Example 5

Human Beta defensin1 and Human Beta defensin2 may be constructed using conventional gene assembly techniques according to the following scheme:
Human Beta defension1: MRTSYLLLFTLCLLLSEMASG-GNFLTGLGHRSDHYNCVSSGGQ-CLYSACPIFTKIQG TCYRGKAKCCK (SEQ ID NO: 14)
Human Beta defensin2: MRVLYLLFSFLFIFLM-PLPGVFGGIGDPVTCLKSGAICHPVFCP RRYK-QIGTCGLPGTKCCKKP (SEQ ID NO: 15).

Example 6

Basic Transcription Factor 3 with structure of: Defensin zinc finger-NAC domain-defensin zinc finger, the Nascent polypeptide-Associated Complex (NAC) domain may be flanked by the defensin zinc fingers using conventional gene assembly techniques: MALSRGTFYFGLALFFIVVELPS-GTCQLKNTLLVQTEANLHTVQQLATLSNRQGQLH LMNNTVSQIRGYWLFQLREQLGAR-CAASMKISCFLLLVLSLSCFQINSVSGIDSVKCF QKNNTCHTIRCPYFQDEVGTCYEGRGKC-CQKRLLSIRVPKKKKLGLNNVSGIEEVN MFTNQG-TAIYFKNPKVQASLAANTFPMTGH-GEIKQLTEMLPSILSHLGADRLTSLRR RAEALPEQSVDGKALLAPGEDNDDEVP-DLVNQAATDQDTAKCVQKKNVCYYFECP WLSIS-VSTCYKGKAKCCQKRY (SEQ ID NO: 19) Epididymal Protein 2, *Homo sapiens*: MKVFFLFAVLFCLVQTNSGD-VPPGIRNTICRMQQ GICRLFFCHSGEKKRDICSDP-WNRCCVSNTDEEGKEKPEMDGRSGI (SEQ ID NO: 20).

Example 7

Alignment of the defensin sequences may be constructed according to the following schemes using conventional gene assembly techniques: SGIDSVKCFQKNNTCHTIRCPY-FQDEVGTCYEGRGKCCQKRTDQDTAKCVQKKNVC YYFECPWLSISVSTCYKGKAKCCQKRY (SEQ ID NO: 21)
Human Beta defensin1: MRTSYLLLFTLCLLLSEMASG-GNFLTGLGHRSDHYNCVSSGGQ-CLYSACPIFTKIQG TCYRGKAKCCK (SEQ ID NO: 14)
Human Beta defensin2: MRVLYLLFSFLFIFLM-PLPGVFGGIGDPVTCLKSGAICH-PVFCPRRYKQIGTCGLPGTK CCKKP (SEQ ID NO: 15)
Epididymal protein 2, *Homo sapiens*: MKVFFLFAVLF-CLVQTNSGDVPPGIRNTICRMQQGICR-LFFCHSGEKKRDICSDPWN RCCVSNTDEEGKEK-PEMDGRSGI (SEQ ID NO: 20).

Example 8

AIDS prognosis has recently been found to relate to defensin levels in the patient (see Cohen, "AIDS research. Mystery Anti-HIV Factor Unmasked?" Science, 297(5590): 2188, 2002).

The HIV has been called "zinc fingers with hubcaps" and has 4 different zinc fingers, including Nucleocapsid P7, integrase, and TAT, and should be quite susceptible to attack with our discovery. In fact in a recent review, 3 of 6 classes of anti-HIV 1 drugs being researched at present target HIV zinc finger peptides (see De Clercq, "New anti-HIV agents and targets," Med. Res. Rev. 22(6): 531-65, 2002).

Virtually all the compounds that are currently used or are subject of advanced clinical trials for the treatment of HIV infections, belong to one of the following classes: . . . (iv) viral assembly and disassembly, through NCp7 zinc finger-targeted agents [2,2'-dithiobisbenzamides (DIBAs), azadicarbonamide (ADA)]; (v) proviral DNA integration, through integrase inhibitors such as 4-aryl-2,4-dioxobutanoic acid derivatives; (vi) viral mRNA transcription, through inhibitors of the transcription (transactivation) process (flavopiridol, fluoroquinolones). See also Buckman et al., "Human immunodeficiency virus type 1 nucleocapsid zn(2+) fingers are required for efficient reverse transcription, initial integration processes, and protection of newly synthesized viral DNA," J. Virol. 77(2): 1469-80, 2003.

Gene therapy using a cassette of appropriate zinc finger defensin genes targeting each of the HIV1 zinc finger protein targets can be designed and inserted, for example in transplanted stem cells. Each of these zinc finger defensin genes can include the appropriate defensin signal sequence.

Injection therapy or very high dose oral therapy with the appropriate anti-HIV1 zinc finger protein defensins could be effective.

For gene therapy, or for direct zinc finger defensin therapy, a mixture of multiple defensins can be used to target and attack multiple sites on the DNA and RNA of the pathogen. This is a key principle and is used in nature, for example in the multiple bovine beta defensins, where changes in the position of the basic R and K residues (see aligned bovine beta defensin sequences below) are used to counter slight changes/variation in target pathogen membrane, and in target pathogen zinc finger DNA and RNA target sequences that would otherwise confer resistance.

Our discovery of the zinc finger nature of defensins now allows rational design of a cassette of multiple defensin genes, or systemic therapy with direct administration of a "cocktail" of multiple but appropriately designed zinc finger defensin proteins, to annihilate the pathogen and its genome.

A45495 . . . DFASCHTNGGICLPNRCPGHMIQIGICFRPRVKCCRSW . . . (SEQ ID NO: 22)
A47753 . . . PEGVRSYLSCWGNRGICLLNRCPGRMRQIGTCLAPRVKCCR . . . (SEQ ID NO: 23)
B45495 . . . VRNHVTCRINRGFCVPIRCPGRTRQIGTCFGPRIKCCRSW . . . (SEQ ID NO: 24)
B47753 . . . GPLSCRRNGGVCIPIRCPGPMRQIGTCFGRPVKCCRSW . . . (SEQ ID NO: 25)
C45495 . . . PEGVRNHVTCRINRGFCVPIRCPGRTRQIGTCFGPRIKCCRSW . . . (SEQ ID NO: 26)
C47753 . . . GPLSCGRNGGVCIPIRCPVPMRQIGTCFGRPVKCCRSW . . . (SEQ ID NO: 27)
D45495 . . . PERVRNPQSCRNMGVCIPFLCRVGMRQIGTCFGPRVPCCRR . . . (SEQ ID NO: 28)
E45495 . . . PEVVRNPQSCRNMGVCIPISCPGNMRQIGTCFGPRVPCCR . . . (SEQ ID NO: 29)
F45495 . . . PEGVRNHVTCRIYGGFCVPIRCPGRTRQIGTCFGRPVKCCRRW. (SEQ ID NO: 30)
G45495 . . . PEGVRNFVTCRINRGFCVPIRCPGHRRQIGTCLGPRIKCCR . . . (SEQ ID NO: 31)
H45495 . . . VRNFVTCRINRGFCVPIRCPGHRRQIGTCLGPQIKCCR . . . (SEQ ID NO: 32)

Selsted et al., "Purification, primary structures, and antibacterial activities of beta-defensins, a new family of antimicrobial peptides from bovine neutrophils," J. Biol. Chem. 268(9): 6641-48, 1993. The in vitro antibacterial activities of the 13 neutrophil peptides, determined in assays using *Staphylococcus aureus* and *Escherichia coli* as test organisms, demonstrated each peptide possessed antimicrobial activity, and that several were as active as the most potent neutrophil defensin, rabbit NP-1.

What is claimed is:

1. An isolated defensin polypeptide comprising helical regions other than the helical regions of the naturally-occurring defensin polypeptide and a zinc finger linker sequence other than the zinc finger linker sequence of the naturally-occurring defensin polypeptide wherein the defensin polypeptide comprises residues 7 through 42 of the amino acid sequence of SEQ ID NO: 13.

2. An isolated defensin polypeptide comprising helical regions other than the helical regions of the naturally-occurring defensin polypeptide and a zinc finger linker sequence other than the zinc finger linker sequence of the naturally-occurring defensin polypeptide wherein the defensin polypeptide comprises the amino acid sequence GLGHRS-DHYNCVSSGDICRLKACHSGEKIQAKCLKNKAKCCK (SEQ ID NO: 13).

* * * * *

SEQUENCE LISTING

```
<160> NUMBER OF SEQ ID NOS: 32

<210> SEQ ID NO 1
<211> LENGTH: 32
<212> TYPE: PRT
<213> ORGANISM: Artificial Sequence
<220> FEATURE:
<223> OTHER INFORMATION: consensus sequence of imperfect repeat from
      Xenopus oocyte transcription factor TFIIIA
<220> FEATURE:
<221> NAME/KEY: misc_feature
<222> LOCATION: (1)..(1)
<223> OTHER INFORMATION: Xaa is Tyr or Phe
<220> FEATURE:
<221> NAME/KEY: misc_feature
<222> LOCATION: (2)..(2)
<223> OTHER INFORMATION: Xaa is any amino acid
<220> FEATURE:
<221> NAME/KEY: misc_feature
<222> LOCATION: (4)..(5)
<223> OTHER INFORMATION: Xaa is any amino acid
<220> FEATURE:
<221> NAME/KEY: misc_feature
<222> LOCATION: (6)..(7)
<223> OTHER INFORMATION: Xaa is any amino acid or is absent
<220> FEATURE:
<221> NAME/KEY: misc_feature
<222> LOCATION: (9)..(11)
<223> OTHER INFORMATION: Xaa is any amino acid
<220> FEATURE:
<221> NAME/KEY: misc_feature
<222> LOCATION: (13)..(17)
<223> OTHER INFORMATION: Xaa is any amino acid
<220> FEATURE:
<221> NAME/KEY: misc_feature
<222> LOCATION: (19)..(20)
<223> OTHER INFORMATION: Xaa is any amino acid
<220> FEATURE:
```

```
<221> NAME/KEY: misc_feature
<222> LOCATION: (22)..(24)
<223> OTHER INFORMATION: Xaa is any amino acid
<220> FEATURE:
<221> NAME/KEY: misc_feature
<222> LOCATION: (25)..(25)
<223> OTHER INFORMATION: Xaa is any amino acid or is absent
<220> FEATURE:
<221> NAME/KEY: misc_feature
<222> LOCATION: (27)..(28)
<223> OTHER INFORMATION: Xaa is any amino acid
<220> FEATURE:
<221> NAME/KEY: misc_feature
<222> LOCATION: (29)..(32)
<223> OTHER INFORMATION: Xaa is any amino acid or is absent

<400> SEQUENCE: 1

Xaa Xaa Cys Xaa Xaa Xaa Xaa Cys Xaa Xaa Phe Xaa Xaa Xaa Xaa
1               5                   10                  15

Xaa Leu Xaa Xaa His Xaa Xaa Xaa Xaa His Xaa Xaa Xaa Xaa Xaa
            20                  25                  30

<210> SEQ ID NO 2
<211> LENGTH: 5
<212> TYPE: PRT
<213> ORGANISM: Artificial Sequence
<220> FEATURE:
<223> OTHER INFORMATION: defensin polypeptide linker region

<400> SEQUENCE: 2

His Thr Gly Glu Lys
1               5

<210> SEQ ID NO 3
<211> LENGTH: 10
<212> TYPE: PRT
<213> ORGANISM: Artificial Sequence
<220> FEATURE:
<223> OTHER INFORMATION: HBD1 sequence-specific DNA and RNA binding
      region

<400> SEQUENCE: 3

Thr Cys Tyr Arg Gly Lys Ala Lys Cys Cys
1               5                   10

<210> SEQ ID NO 4
<211> LENGTH: 5
<212> TYPE: PRT
<213> ORGANISM: Artificial Sequence
<220> FEATURE:
<223> OTHER INFORMATION: zinc finger linker region
<220> FEATURE:
<221> NAME/KEY: misc_feature
<222> LOCATION: (5)..(5)
<223> OTHER INFORMATION: Xaa is Pro or is absent

<400> SEQUENCE: 4

Thr Gly Glu Lys Xaa
1               5

<210> SEQ ID NO 5
<211> LENGTH: 96
<212> TYPE: PRT
<213> ORGANISM: Artificial Sequence
<220> FEATURE:
<223> OTHER INFORMATION: Pyrimidine Pathway Regulator

<400> SEQUENCE: 5

Met Lys Ser Arg Thr Ala Cys Lys Arg Cys Arg Leu Lys Lys Ile Lys
1               5                   10                  15
```

```
Cys Asp Gln Glu Phe Pro Ser Cys Lys Arg Cys Ala Lys Leu Glu Val
                20                  25                  30

Pro Cys Val Ser Leu Asp Pro Ala Thr Gly Lys Asp Val Pro Arg Ser
            35                  40                  45

Tyr Val Phe Phe Leu Glu Asp Arg Leu Ala Val Met Met Arg Val Leu
        50                  55                  60

Lys Glu Tyr Gly Val Asp Pro Thr Lys Ile Arg Gly Asn Ile Pro Ala
65                  70                  75                  80

Thr Ser Asp Asp Glu Pro Phe Asp Leu Lys Lys Tyr Ser Ser Val Ser
                85                  90                  95

<210> SEQ ID NO 6
<211> LENGTH: 28
<212> TYPE: PRT
<213> ORGANISM: Artificial Sequence
<220> FEATURE:
<223> OTHER INFORMATION: Gal4 zinc finger region

<400> SEQUENCE: 6

Cys Asp Ile Cys Arg Leu Lys Lys Leu Lys Cys Ser Lys Glu Lys Pro
1               5                   10                  15

Lys Cys Ala Lys Cys Leu Lys Asn Asn Trp Glu Cys
            20                  25

<210> SEQ ID NO 7
<211> LENGTH: 6
<212> TYPE: PRT
<213> ORGANISM: Artificial Sequence
<220> FEATURE:
<223> OTHER INFORMATION: Gal4 helical region

<400> SEQUENCE: 7

Asp Ile Cys Arg Leu Lys
1               5

<210> SEQ ID NO 8
<211> LENGTH: 6
<212> TYPE: PRT
<213> ORGANISM: Artificial Sequence
<220> FEATURE:
<223> OTHER INFORMATION: Gal4 helical region

<400> SEQUENCE: 8

Ala Lys Cys Leu Lys Asn
1               5

<210> SEQ ID NO 9
<211> LENGTH: 5
<212> TYPE: PRT
<213> ORGANISM: Artificial Sequence
<220> FEATURE:
<223> OTHER INFORMATION: zinc finger linker region

<400> SEQUENCE: 9

His Ser Gly Glu Lys
1               5

<210> SEQ ID NO 10
<211> LENGTH: 31
<212> TYPE: PRT
<213> ORGANISM: Artificial Sequence
<220> FEATURE:
<223> OTHER INFORMATION: zinc finger linker sequence of epididymal
      protein 2 sperm associated antigen defensin
```

-continued

```
<400> SEQUENCE: 10

Cys Arg Met Gln Gln Gly Ile Cys Arg Leu Phe Phe Cys His Ser Gly
1               5                   10                  15

Glu Lys Lys Arg Asp Ile Cys Ser Asp Pro Trp Asn Arg Cys Cys
            20                  25                  30

<210> SEQ ID NO 11
<211> LENGTH: 6
<212> TYPE: PRT
<213> ORGANISM: Artificial Sequence
<220> FEATURE:
<223> OTHER INFORMATION: zinc finger DNA interacting region

<400> SEQUENCE: 11

Gly Gln Cys Leu Tyr Ser
1               5

<210> SEQ ID NO 12
<211> LENGTH: 6
<212> TYPE: PRT
<213> ORGANISM: Artificial Sequence
<220> FEATURE:
<223> OTHER INFORMATION: zinc finger DNA interacting region

<400> SEQUENCE: 12

Gly Thr Cys Tyr Arg Gly
1               5

<210> SEQ ID NO 13
<211> LENGTH: 42
<212> TYPE: PRT
<213> ORGANISM: Artificial Sequence
<220> FEATURE:
<223> OTHER INFORMATION: antifungal pyrimidine pathway suppressor

<400> SEQUENCE: 13

Gly Leu Gly His Arg Ser Asp His Tyr Asn Cys Val Ser Ser Gly Asp
1               5                   10                  15

Ile Cys Arg Leu Lys Ala Cys His Ser Gly Glu Lys Ile Gln Ala Lys
            20                  25                  30

Cys Leu Lys Asn Lys Ala Lys Cys Cys Lys
        35                  40

<210> SEQ ID NO 14
<211> LENGTH: 68
<212> TYPE: PRT
<213> ORGANISM: Homo sapiens

<400> SEQUENCE: 14

Met Arg Thr Ser Tyr Leu Leu Leu Phe Thr Leu Cys Leu Leu Leu Ser
1               5                   10                  15

Glu Met Ala Ser Gly Gly Asn Phe Leu Thr Gly Leu Gly His Arg Ser
            20                  25                  30

Asp His Tyr Asn Cys Val Ser Ser Gly Gly Gln Cys Leu Tyr Ser Ala
        35                  40                  45

Cys Pro Ile Phe Thr Lys Ile Gln Gly Thr Cys Tyr Arg Gly Lys Ala
    50                  55                  60

Lys Cys Cys Lys
65

<210> SEQ ID NO 15
<211> LENGTH: 64
<212> TYPE: PRT
```

<213> ORGANISM: Homo sapiens

<400> SEQUENCE: 15

Met Arg Val Leu Tyr Leu Leu Phe Ser Phe Leu Ile Phe Leu Met
1               5                   10                  15

Pro Leu Pro Gly Val Phe Gly Gly Ile Gly Asp Pro Val Thr Cys Leu
            20                  25                  30

Lys Ser Gly Ala Ile Cys His Pro Val Phe Cys Pro Arg Arg Tyr Lys
        35                  40                  45

Gln Ile Gly Thr Cys Gly Leu Pro Gly Thr Lys Cys Cys Lys Lys Pro
    50                  55                  60

<210> SEQ ID NO 16
<211> LENGTH: 29
<212> TYPE: PRT
<213> ORGANISM: Artificial Sequence
<220> FEATURE:
<223> OTHER INFORMATION: pyrimidine pathway regulator zinc finger

<400> SEQUENCE: 16

Cys Lys Arg Cys Arg Leu Lys Lys Ile Lys Cys Asp Gln Glu Phe Pro
1               5                   10                  15

Ser Cys Lys Arg Cys Ala Lys Leu Glu Val Pro Cys Val
            20                  25

<210> SEQ ID NO 17
<211> LENGTH: 4
<212> TYPE: PRT
<213> ORGANISM: Artificial Sequence
<220> FEATURE:
<223> OTHER INFORMATION: defensin region

<400> SEQUENCE: 17

Ser Gly Glu Lys
1

<210> SEQ ID NO 18
<211> LENGTH: 4
<212> TYPE: PRT
<213> ORGANISM: Artificial Sequence
<220> FEATURE:
<223> OTHER INFORMATION: defensin region

<400> SEQUENCE: 18

Thr Gly Glu Lys
1

<210> SEQ ID NO 19
<211> LENGTH: 304
<212> TYPE: PRT
<213> ORGANISM: Homo sapiens

<400> SEQUENCE: 19

Met Ala Leu Ser Arg Gly Thr Phe Tyr Phe Gly Leu Ala Leu Phe Phe
1               5                   10                  15

Ile Val Val Glu Leu Pro Ser Gly Thr Cys Gln Leu Lys Asn Thr Leu
            20                  25                  30

Leu Val Gln Thr Glu Ala Asn Leu His Thr Val Gln Gln Leu Ala Thr
        35                  40                  45

Leu Ser Asn Arg Gln Gly Gln Leu His Leu Met Asn Asn Thr Val Ser
    50                  55                  60

Gln Ile Arg Gly Tyr Trp Leu Phe Gln Leu Arg Glu Gln Leu Gly Ala
65                  70                  75                  80

```
Arg Cys Ala Ala Ser Met Lys Ile Ser Cys Phe Leu Leu Val Leu
                85                  90                  95

Ser Leu Ser Cys Phe Gln Ile Asn Ser Val Ser Gly Ile Asp Ser Val
            100                 105                 110

Lys Cys Phe Gln Lys Asn Asn Thr Cys His Thr Ile Arg Cys Pro Tyr
        115                 120                 125

Phe Gln Asp Glu Val Gly Thr Cys Tyr Glu Gly Arg Gly Lys Cys Cys
    130                 135                 140

Gln Lys Arg Leu Leu Ser Ile Arg Val Pro Lys Lys Lys Leu Gly
145                 150                 155                 160

Leu Asn Asn Val Ser Gly Ile Glu Glu Val Asn Met Phe Thr Asn Gln
                165                 170                 175

Gly Thr Ala Ile Tyr Phe Lys Asn Pro Lys Val Gln Ala Ser Leu Ala
            180                 185                 190

Ala Asn Thr Phe Pro Met Thr Gly His Gly Glu Ile Lys Gln Leu Thr
        195                 200                 205

Glu Met Leu Pro Ser Ile Leu Ser His Leu Gly Ala Asp Arg Leu Thr
    210                 215                 220

Ser Leu Arg Arg Arg Ala Glu Ala Leu Pro Glu Gln Ser Val Asp Gly
225                 230                 235                 240

Lys Ala Leu Leu Ala Pro Gly Glu Asp Asn Asp Glu Val Pro Asp
                245                 250                 255

Leu Val Asn Gln Ala Ala Thr Asp Gln Asp Thr Ala Lys Cys Val Gln
            260                 265                 270

Lys Lys Asn Val Cys Tyr Tyr Phe Glu Cys Pro Trp Leu Ser Ile Ser
        275                 280                 285

Val Ser Thr Cys Tyr Lys Gly Lys Ala Lys Cys Cys Lys Arg Tyr
    290                 295                 300

<210> SEQ ID NO 20
<211> LENGTH: 80
<212> TYPE: PRT
<213> ORGANISM: Homo sapiens

<400> SEQUENCE: 20

Met Lys Val Phe Phe Leu Phe Ala Val Leu Phe Cys Leu Val Gln Thr
1               5                   10                  15

Asn Ser Gly Asp Val Pro Pro Gly Ile Arg Asn Thr Ile Cys Arg Met
            20                  25                  30

Gln Gln Gly Ile Cys Arg Leu Phe Cys His Ser Gly Glu Lys Lys
        35                  40                  45

Arg Asp Ile Cys Ser Asp Pro Trp Asn Arg Cys Cys Val Ser Asn Thr
    50                  55                  60

Asp Glu Glu Gly Lys Glu Lys Pro Glu Met Asp Gly Arg Ser Gly Ile
65                  70                  75                  80

<210> SEQ ID NO 21
<211> LENGTH: 83
<212> TYPE: PRT
<213> ORGANISM: Artificial Sequence
<220> FEATURE:
<223> OTHER INFORMATION: defensin sequence

<400> SEQUENCE: 21

Ser Gly Ile Asp Ser Val Lys Cys Phe Gln Lys Asn Asn Thr Cys His
1               5                   10                  15

Thr Ile Arg Cys Pro Tyr Phe Gln Asp Glu Val Gly Thr Cys Tyr Glu
```

```
            20                  25                  30
Gly Arg Gly Lys Cys Cys Gln Lys Arg Thr Asp Gln Asp Thr Ala Lys
        35                  40                  45

Cys Val Gln Lys Lys Asn Val Cys Tyr Tyr Phe Glu Cys Pro Trp Leu
    50                  55                  60

Ser Ile Ser Val Ser Thr Cys Tyr Lys Gly Lys Ala Lys Cys Cys Gln
65                  70                  75                  80

Lys Arg Tyr

<210> SEQ ID NO 22
<211> LENGTH: 38
<212> TYPE: PRT
<213> ORGANISM: Bos taurus

<400> SEQUENCE: 22

Asp Phe Ala Ser Cys His Thr Asn Gly Gly Ile Cys Leu Pro Asn Arg
1               5                   10                  15

Cys Pro Gly His Met Ile Gln Ile Gly Ile Cys Phe Arg Pro Arg Val
                20                  25                  30

Lys Cys Cys Arg Ser Trp
        35

<210> SEQ ID NO 23
<211> LENGTH: 41
<212> TYPE: PRT
<213> ORGANISM: Bos Taurus

<400> SEQUENCE: 23

Pro Glu Gly Val Arg Ser Tyr Leu Ser Cys Trp Gly Asn Arg Gly Ile
1               5                   10                  15

Cys Leu Leu Asn Arg Cys Pro Gly Arg Met Arg Gln Ile Gly Thr Cys
                20                  25                  30

Leu Ala Pro Arg Val Lys Cys Cys Arg
            35                  40

<210> SEQ ID NO 24
<211> LENGTH: 40
<212> TYPE: PRT
<213> ORGANISM: Bos Taurus

<400> SEQUENCE: 24

Val Arg Asn His Val Thr Cys Arg Ile Asn Arg Gly Phe Cys Val Pro
1               5                   10                  15

Ile Arg Cys Pro Gly Arg Thr Arg Gln Ile Gly Thr Cys Phe Gly Pro
                20                  25                  30

Arg Ile Lys Cys Cys Arg Ser Trp
            35                  40

<210> SEQ ID NO 25
<211> LENGTH: 38
<212> TYPE: PRT
<213> ORGANISM: Bos taurus

<400> SEQUENCE: 25

Gly Pro Leu Ser Cys Arg Arg Asn Gly Gly Val Cys Ile Pro Ile Arg
1               5                   10                  15

Cys Pro Gly Pro Met Arg Gln Ile Gly Thr Cys Phe Gly Arg Pro Val
                20                  25                  30

Lys Cys Cys Arg Ser Trp
        35
```

<210> SEQ ID NO 26
<211> LENGTH: 43
<212> TYPE: PRT
<213> ORGANISM: Bos taurus

<400> SEQUENCE: 26

Pro Glu Gly Val Arg Asn His Val Thr Cys Arg Ile Asn Arg Gly Phe
1               5                   10                  15

Cys Val Pro Ile Arg Cys Pro Gly Arg Thr Arg Gln Ile Gly Thr Cys
                20                  25                  30

Phe Gly Pro Arg Ile Lys Cys Cys Arg Ser Trp
            35                  40

<210> SEQ ID NO 27
<211> LENGTH: 38
<212> TYPE: PRT
<213> ORGANISM: Bos taurus

<400> SEQUENCE: 27

Gly Pro Leu Ser Cys Gly Arg Asn Gly Gly Val Cys Ile Pro Ile Arg
1               5                   10                  15

Cys Pro Val Pro Met Arg Gln Ile Gly Thr Cys Phe Gly Arg Pro Val
                20                  25                  30

Lys Cys Cys Arg Ser Trp
            35

<210> SEQ ID NO 28
<211> LENGTH: 42
<212> TYPE: PRT
<213> ORGANISM: Bos taurus

<400> SEQUENCE: 28

Pro Glu Arg Val Arg Asn Pro Gln Ser Cys Arg Trp Asn Met Gly Val
1               5                   10                  15

Cys Ile Pro Phe Leu Cys Arg Val Gly Met Arg Gln Ile Gly Thr Cys
                20                  25                  30

Phe Gly Pro Arg Val Pro Cys Cys Arg Arg
            35                  40

<210> SEQ ID NO 29
<211> LENGTH: 41
<212> TYPE: PRT
<213> ORGANISM: Bos taurus

<400> SEQUENCE: 29

Pro Glu Val Val Arg Asn Pro Gln Ser Cys Arg Trp Asn Met Gly Val
1               5                   10                  15

Cys Ile Pro Ile Ser Cys Pro Gly Asn Met Arg Gln Ile Gly Thr Cys
                20                  25                  30

Phe Gly Pro Arg Val Pro Cys Cys Arg
            35                  40

<210> SEQ ID NO 30
<211> LENGTH: 43
<212> TYPE: PRT
<213> ORGANISM: Bos taurus

<400> SEQUENCE: 30

Pro Glu Gly Val Arg Asn His Val Thr Cys Arg Ile Tyr Gly Gly Phe
1               5                   10                  15

-continued

```
Cys Val Pro Ile Arg Cys Pro Gly Arg Thr Arg Gln Ile Gly Thr Cys
            20                  25                  30

Phe Gly Arg Pro Val Lys Cys Cys Arg Arg Trp
        35                  40

<210> SEQ ID NO 31
<211> LENGTH: 41
<212> TYPE: PRT
<213> ORGANISM: Bos taurus

<400> SEQUENCE: 31

Pro Glu Gly Val Arg Asn Phe Val Thr Cys Arg Ile Asn Arg Gly Phe
1               5                   10                  15

Cys Val Pro Ile Arg Cys Pro Gly His Arg Arg Gln Ile Gly Thr Cys
            20                  25                  30

Leu Gly Pro Arg Ile Lys Cys Cys Arg
        35                  40

<210> SEQ ID NO 32
<211> LENGTH: 38
<212> TYPE: PRT
<213> ORGANISM: Bos taurus

<400> SEQUENCE: 32

Val Arg Asn Phe Val Thr Cys Arg Ile Asn Arg Gly Phe Cys Val Pro
1               5                   10                  15

Ile Arg Cys Pro Gly His Arg Arg Gln Ile Gly Thr Cys Leu Gly Pro
            20                  25                  30

Gln Ile Lys Cys Cys Arg
        35
```